United States Patent [19]

Baghel et al.

[11] Patent Number: 5,382,736
[45] Date of Patent: Jan. 17, 1995

[54] METHOD FOR CATALYTIC DECHLORINATION OF POLYCHLORINATED BIPHENYLS

[75] Inventors: Sunita S. Baghel, Rensselaer; Deborah A. Haitko, Schenectady, both of N.Y.

[73] Assignee: General Electric Company, Schenectady, N.Y.

[21] Appl. No.: 55,092

[22] Filed: May 3, 1993

[51] Int. Cl.$^6$ ............ C07C 1/20; C07C 7/00; C10G 17/00; C10G 45/00
[52] U.S. Cl. .................... 585/469; 585/841; 585/864; 585/860; 208/262.1; 208/262.5; 423/481
[58] Field of Search ......... 585/469, 841, 864, 860; 208/262.1, 262.5; 423/481

[56] References Cited

U.S. PATENT DOCUMENTS

| | | | |
|---|---|---|---|
| 4,022,795 | 5/1977 | Bamfield et al. | 585/427 |
| 4,618,686 | 10/1986 | Boyer . | |
| 4,950,833 | 8/1990 | Hawari et al. | 585/469 |
| 4,973,783 | 11/1990 | Griller et al. | 585/469 |
| 5,015,457 | 5/1991 | Langhoff et al. | 423/481 |
| 5,019,175 | 5/1991 | Rogers et al. | 585/469 |
| 5,141,629 | 8/1992 | Pri-Bar et al. | 585/469 |

OTHER PUBLICATIONS

Article–J. Org. Chem., vol. 56, No. 21 (1991)–Transfer Hydrogenolysis of Aryl Halides and Other Hydrogen Acceptors by Formate Salts in the Presence of Pd/C Catalyst, H. Wiener et al, pp. 6145–6147.

*Primary Examiner*—Helen M. S. Sneed
*Assistant Examiner*—E. D. Irzinski
*Attorney, Agent, or Firm*—James Magee, Jr.

[57] ABSTRACT

An improved method for the dechlorination of polychlorinated biphenyls that are dissolved in an organic solvent, which comprises the incremental additions of a hydrogen transfer agent, such as potassium formate, in the presence of a catalytic amount of a hydrogenation catalyst, such as palladium supported on carbon, and water.

10 Claims, 1 Drawing Sheet

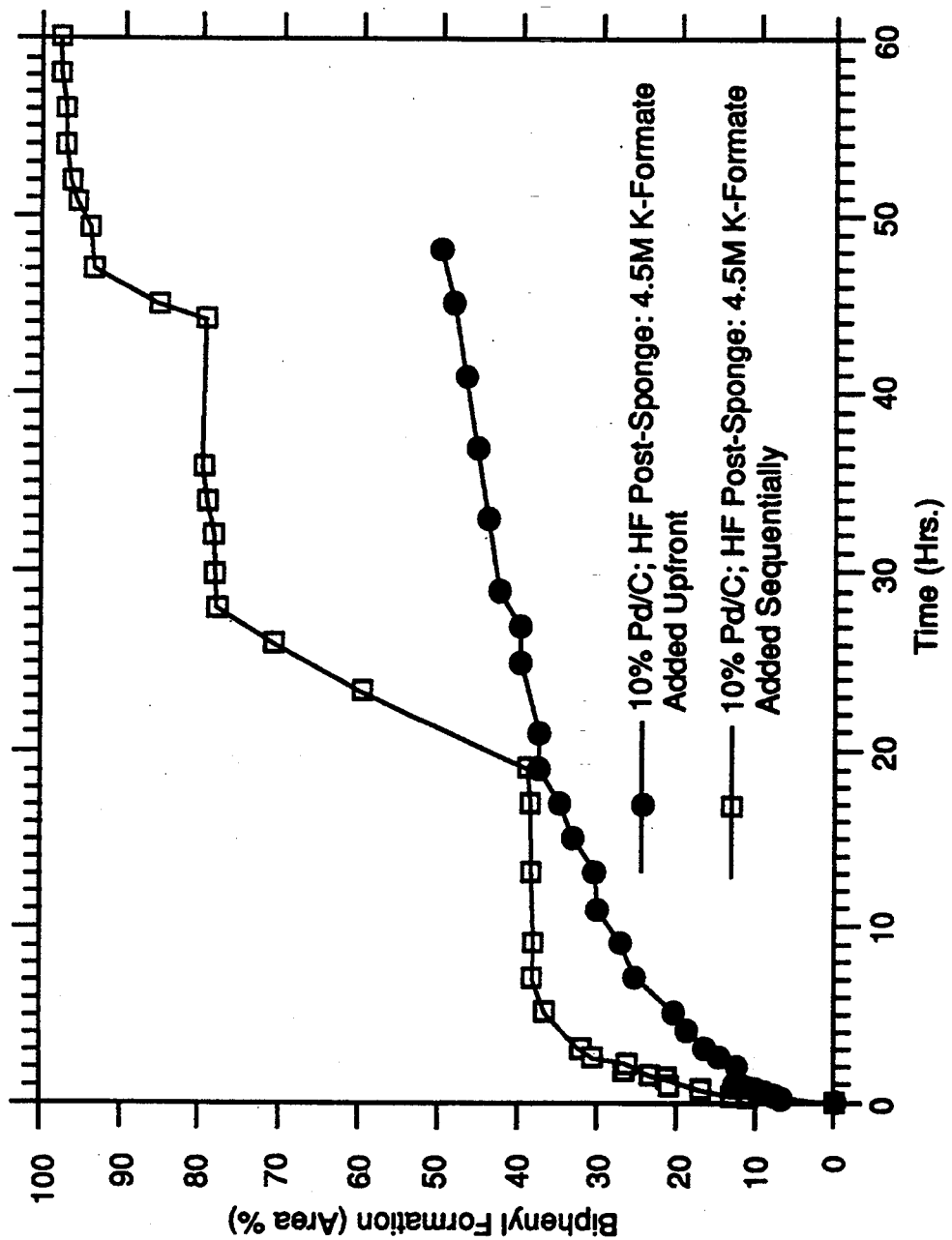

METHOD FOR CATALYTIC DECHLORINATION OF POLYCHLORINATED BIPHENYLS

FIELD OF THE INVENTION

This invention relates to a method for catalytic dechlorination of polychlorinated biphenyls, dissolved in an organic solvent, and more particularly, to the substantially complete formation of biphenyl by the incremental additions of a hydrogen transfer agent in the presence of a catalytic amount of a hydrogenation catalyst and water.

BACKGROUND OF THE INVENTION

The chemical structure of polychlorinated biphenyls has been known for nearly 100 years. Commercial production was initiated in the United States in 1929 in response to the electrical industry's need for an improved dielectric insulating fluid for use in transformers and capacitors which would also provide increased fire resistant benefits.

The fire resistant nature of the polychlorinated biphenyls, combined with outstanding thermal stability made them excellent choices as hydraulic and heat transfer fluids alone or in formulations. They were also used to improve the waterproofing characteristics of surface coatings and offered many advantages to the manufacturer of carbonless copy paper, printing inks, plasticizers, special adhesives, lubricating additives, and vacuum pump fluids.

In the late 1960s, the first signs of polychlorinated biphenyls' potential environmental problems appeared. A Swedish biologist identified polychlorinated biphenyls as interference peaks in DDT determinations in the bodies of fish.

Since then, scientific investigations confirmed the presence of polychlorinated biphenyls in the environment in the United States. In the 1970s, Monsanto, as the sole U.S. manufacturer of polychlorinated biphenyls, voluntarily began a program to terminate sales of polychlorinated biphenyls for those applications that were likely to result in environmental contamination. By late 1976, Monsanto made arrangements to completely withdraw from the manufacture of polychlorinated biphenyls.

Because of their thermal and chemical stability and non-reactive nature, polychlorinated biphenyls tend to accumulate and persist in the environment. As the result of improved analytical techniques, polychlorinated biphenyls have been found in many places in the United States and have found their way into all levels of the food chain. Due to the known toxic effects of polychlorinated biphenyls, governmental actions have resulted in the control of the use, disposal, and production of polychlorinated biphenyls in nearly all world areas, including the United States. Thus, there is a need for an efficient and economic method for removing polychlorinated biphenyls from the environment.

It is known that polychlorinated biphenyls can be reduced to non-toxic biphenyls by catalytic dechlorination utilizing a hydrogenation catalyst and a hydrogen transfer donor. Typical hydrogen donors reported in the literature for this application are formic acid, hydrogen, ammonium formate, and sodium hypophosphite.

Potassium formate and sodium formate are the preferred hydrogen donors for the reduction of polychlorinated biphenyls. This is based on the fact that these salts are true hydrogen transfer agents, as no hydrogen gas is released in the course of the reactions. Hydrogen evolution is, in fact, the main limitation associated with the utilization of ammonium formate and other hydrogen donors, such as sodium hypophosphite.

Palladium supported on carbon is the most popular hydrogenation catalyst that is used for this application. There are studies using different supports for palladium, such as alumina, silica gel, calcium carbonate, and barium sulfate. There are also studies using homogeneous catalysts, such as palladium tetrakistriphenylphosphine.

It is also known that Raney nickel and platinum can be used as hydrogenation catalysts, either supported on other carriers or non-supported.

It has been demonstrated that the dechlorination of polychlorinated biphenyls, utilizing a hydrogenation catalyst and hydrogen transfer agent, is very sensitive to the concentration of water present in the system. The effect of water is attributed to the fact that water is an actual reactant in the hydrogen-transfer process and it has to compete with the other two substrates for an adsorption site on the catalyst surface. Further, it has been shown that the maximum rate is obtained when the water/formate molar ratio is about 3.

Catalytic dechlorination of pure samples of polychlorinated biphenyls, using palladium supported on carbon and potassium formate or sodium formate coupled with water as hydrogen transfer agents, proceeds readily in a variety of alcohols. However, the rate and extent of dechlorination diminishes when a polychlorinated biphenyl solution is taken from an actual environmental site.

Due to the presence of other contaminants in combination with polychlorinated biphenyls in the environment, the dechlorination reaction does not proceed to completion. It is known that one way to complete the dechlorination of an environmental sample is to add excess palladium supported on carbon. Thus, there is a need to develop an improved method of catalytic dechlorination of polychlorinated biphenyls that are generated from the environment. Such a method is needed to insure that the dechlorination of polychlorinated biphenyls proceeds readily to completion without the addition of excess palladium supported on carbon.

SUMMARY OF THE INVENTION

Generally speaking, this invention fulfills these needs by providing a method for dechlorination of polychlorinated biphenyls which comprises the dissolution of a polychlorinated biphenyl in an organic solvent and contacting the solution with a catalytic amount of a hydrogenation catalyst in the presence of water, followed by incremental additions of a hydrogen transfer agent.

Hydrogen transfer agents, in general, are useful in the practice of this invention. Such agents function as a source of hydrogen in a catalyst mediated reaction, which transfers hydrogen from the transfer agent to the polychlorinated biphenyl compound with resulting removal of chlorine and replacement by a hydrogen atom. A highly preferred class of hydrogen transfer agents are those which do not evolve molecular hydrogen during the course of the reaction. Examples of such non-hydrogen evolving transfer agents include the formate salts of cesium, lithium, potassium, and sodium. Sodium formate and potassium formate are particularly preferred hydrogen transfer agents for use in this invention.

The method can be used for pure polychlorinated biphenyl contaminants and for polychlorinated biphenyls obtained from the environment. The polychlorinated biphenyl is dissolved in a suitable organic solvent, such as propanol; in an oil, such as mineral oil; in a mixture of solvent—water; or in a mixture of oil—water. Surfactants, either nonionic or ionic, may be present in the mixture.

This method is characterized by an increased reaction rate and the substantially complete dechlorination of polychlorinated biphenyls through the incremental addition of a molar excess of a hydrogen transfer agent to the reaction.

Another embodiment of the reaction is the dechlorination of polychlorinated biphenyls obtained from the environment in the presence of other contaminants.

This method is further enhanced by the use of a molar excess of a hydrogen transfer agent rather than further additions to the reaction of hydrogenation catalysts.

BRIEF DESCRIPTION OF DRAWINGS

FIG. 1 is a graph depicting the biphenyl formation (area %) vs. time of formation, which demonstrates the degree of completion of the reaction based on incremental additions of potassium formate and a batch addition of potassium formate, each using 10% palladium supported on carbon.

DETAILED DESCRIPTION OF THE INVENTION

The present invention is a method for the substantially complete dechlorination of polychlorinated biphenyls which utilizes a hydrogenation catalyst in the presence of water and an organic solvent, followed by the incremental addition of a hydrogen transfer agent. Such method is applied to pure samples of polychlorinated biphenyl contaminants and polychlorinated biphenyls from the environment.

Polychlorinated biphenyls are commonly known as PCBs. The U.S. Environmental Protection Agency has defined as PCB contaminated: any material containing more than 50 ppm of a mono-, di-, or polychlorinated biphenyl. Such PCB contaminated materials may be efficiently and economically dechlorinated with the instant process to yield nonchlorinated biphenyls.

The reaction medium is an organic-aqueous mixture. The organic solvent can be an alcohol or a dipolar aprotic solvent.

The alcohol medium is selected from a group consisting of alcohols having 1 to about 8 carbons and up to two hydroxy groups, such as ethylene glycol. Propanol and ethanol are the organic solvents of choice. The most preferred organic solvent is isopropyl alcohol.

The reaction can also be carried out in dipolar aprotic solvents. A dipolar aprotic solvent is a substance which acts as neither an acid or a base. Examples of dipolar aprotic solvents that may be used are acetonitrile or dimethylsulfone.

The ratio of the water to the organic solvent is at least about 5% by weight water with the balance being the organic solvent. The preferred ratio of water to organic solvent is about 12% to about 15% by weight water with the balance being organic solvent.

The reaction medium can also be an oil-water mixture in which the oil can be mineral oil, transformer oil, or an askarel oil. Askarel oil is the generic name for a chlorinated diphenyl oil. The ratio of the water to the oil is at least about 5% by weight water with the balance being oil. The range of the ratio of the water to the oil is about 5% to about 95% by weight water. The preferred ratio is about 50% by weight water with the balance being oil.

The polychlorinated biphenyls are dissolved in the organic-water mixture by stirring at room temperature and ambient pressure. Use of a surface active agent to facilitate dissolution is optional. The surface active agent may be an ionic or nonionic surfactant. An example of an ionic surface active agent is a sodium dodecylbenzenesulfonate. An example of a nonionic surface active agent is a polyethoxylated decyl alcohol.

If the alcohol solvent is distilled away during the course of the reaction, so that the remaining mixture contains a surfactant-oil-water mixture, the reaction will still proceed to completion by the formation of biphenyls.

To the polychlorinated biphenyl-organic solvent mixture, an appropriate amount of base is added so as to maintain the pH of the solution between about 7.0 and about 10.0. If the hydrogen transfer agent is sodium formate, the preferred base is sodium hydroxide. The preferred base is potassium hydroxide if the hydrogen transfer agent is potassium formate.

The metal hydrogenation catalysts useful in the practice of this invention include palladium, platinum, and Raney nickel. The preferred catalyst is palladium. It is advantageous if the catalyst is carried on a suitable support, preferably carbon.

The bond ratio between the palladium atom and the chlorine-carbon bond is about 1:1 (Pd:C—Cl) to about 1:600 (Pd:C—Cl). The preferred bond ratio between palladium and carbon-chlorine is about 1:111. The palladium to carbon-chlorine bond ratio is determined based upon the percent chlorine present within the polychlorinated biphenyl. For example, one gram of Aroclor 1254 contains 54% chlorine or 0.54 grams of chlorine. The molar amount would be 0.54 grams divided by the molecular weight of chlorine, approximately 35.45 grams, to give 0.0152 moles of chlorine or carbon-chlorine bonds for one gram of Aroclor 1254. To obtain a carbon-chlorine bond ratio of Aroclor 1254 to palladium of 111 to 1, approximately 0.13 millimoles of palladium are required or approximately 0.138 grams of 10% palladium on carbon.

A catalytic amount of the hydrogenation catalyst is added at the beginning of the reaction. Subsequent additions of the hydrogenation catalyst are not required.

The preferred hydrogen transfer agent is sodium formate or potassium formate. An excess molar amount of sodium formate or potassium formate is added in increments based on the degree of chlorination. The excess molar amount of sodium formate or potassium formate is between 1.5 and 6.5.

Approximately equal incremental amounts of the hydrogen transfer agent are added to the reaction in two or three additions, with three additions being preferred. The term "incremental amount" means a fixed amount of the hydrogen transfer agent which is calculated by dividing the total excess molar amount of the hydrogen transfer agent by the number of additions to be made to the reaction. Each incremental amount is added in an equal portion at a designated time interval which is determined by monitoring the progress of the reaction. High pressure liquid chromatography, herein known as HPLC, is used to monitor the dechlorination of the polycholorinated biphenyls.

The total excess molar amount of the hydrogen transfer agent is based upon the number of C—Cl bonds present. Up to a 20 molar excess amount of excess hydrogen transfer reagent may be used. A 4.5 molar excess amount of the hydrogen transfer agent is preferred.

The initial increment of sodium formate or potassium formate is dissolved in water (about 5.0 grams) and added to the mixture at room temperature with vigorous stirring. Rapid stirring is essential to hasten the rate of the reaction and to insure contact of the phases. Also, since the reaction is typically exothermic, the hydrogen transfer agent is added in a controlled fashion to reduce excessive heating of the reaction medium.

Once all of the reactants and catalyst are mixed, it is preferred to have agitation in the reaction vessel while heat is applied. The temperature of the bath is between 60° C. and 80° C. with the preferred temperature being 70° C. The reaction can proceed at room temperature, but due to the longer time for reaction completion, it is not recommended.

After an initial period of time, the reaction vessel is removed from the oil bath and allowed to cool to room temperature. A subsequent addition of the hydrogen transfer agent is then added dry to the cooled medium. Upon addition of the transfer agent, the reaction vessel is again heated to about 60° C. to about 80° C.

After a period of time the third addition of dry hydrogen transfer agent is made to the reaction at room temperature. The reaction is then continued at 60° C. to 80° C. until the substantially complete formation of biphenyl product.

The dechlorination of the polychlorinated biphenyls is confirmed by HPLC. The HPLC conditions used to follow the catalytic dechlorination reactions include use of a Dupont Instrument 8800 High Pressure Liquid Chromatography System equipped with a reverse phase Whatman Partisil ODS-3, C-18 column. A linear solvent gradient was employed with an initial concentration of water-acetonitrile mixture of approximately 55/45 respectively, and a final concentration of 100% acetonitrile with a total analysis time of 25 minutes. The reaction was monitored at 254 nm.

Another detecting technique, gas chromatography, herein GC, was also employed in confirming the dechlorination of the polychlorinated biphenyls by the process of the present invention. The gas chromatography analysis was coupled with electron capture detection and was done at Northeast Analytical located in Schenectady, New York.

The following examples are presented only for purposes of illustration and are not intended to limit the scope of the invention. Many other improvements may become apparent to the skilled artisan after reading the patent application and those improvements are considered to be a part of the present invention.

EXAMPLE 1

All materials were used as received. Potassium formate was obtained from Fluka Chemika in Ronkonkoma, N.Y., (>99.0% purity), 10% palladium on carbon was obtained from Aldrich in Milwaukee, Wisconsin (98% purity), Aroclor 1242 from Accustandard in New Haven, Conn., and Renex® KB from ICI Specialty Chemicals in Wilmington, Del. with the tradename Renex® KB=Synthrapol® KB or a polyethoxylated decyl alchohol, $C_{10}H_{21}(CH_2CH_2O)_xH$; x=5.5 avg.; with the hydrophilic lipophilic balance, herein HLB, equals 12.1. Progress of the catalytic dechlorination was followed by HPLC.

DEHALOGENATION OF POLYCHLORINATED BIPHENYLS BY INCREMENTAL ADDITION OF POTASSIUM FORMATE

A three-necked 100 ml round-bottomed equipped with an overhead mechanical paddle (teflon) stirrer, thermometer, and water-cooled condenser fitted with a nitrogen inlet was initially charged with 40.0 grams of Hudson Falls (Aroclor) post-organic sponge regenerated sample in 2-propanol, potassium formate (0.257 gm, 3.0 mmol -1.5 molar excess based upon C—Cl bonds), potassium hydroxide (0.1.gm, 1.8 mmol), and water (5.0 gm, 0.28 mol). The reaction was stirred at room temperature until complete dissolution of the base had been accomplished. The point at which the solution was homogenous was labelled time=0 for kinetic purposes. A sample was taken, 0.2 ml, and diluted with 2.0 ml acetonitrile prior to HPLC analysis. The 10% palladium on carbon (0.018 gm, 0.017 mmol; 1 Pd=111 C—Cl) was added to the flask at room temperature. After the addition of the palladium on carbon, the flask was emersed into a 70° C. oil bath. The reaction was sampled every 15 minutes for the first two hours and then samples were subsequently taken every two hours. Reaction progress was monitored by formation of biphenyl using HPLC analysis. Approximately 39% biphenyl formation was seen within the first 7 hours. After 21 hours at 70° C., the reaction was cooled and the second addition of potassium formate (0.257 gm, 3.0 mmol) was made. After 44 hours the biphenyl formation had reached approximately 80% overall without adding any palladium on carbon. The third and fourth additions of potassium formate (0.256 gm, 3.0 mmol) were made at the 45 and 50 hour points, respectively. At the 50 hour point approximately 97,4% biphenyl formation was detected by HPLC analysis. The reaction was allowed to reflux for 60 hours before cooling to room temperature. The final analysis of the reaction solution was performed by gas chromatography coupled with electron capture detection at Northeast Analytical located in Schenectady, N.Y. and was 3.8 ppm polychlorinated biphenyls.

EXAMPLE 2

DECHLORINATION OF POLYCHLORINATED BIPHENYLS BY TOTAL INITIAL ADDITION OF POTASSIUM FORMATE

A three-necked 100 ml round-bottomed flask equipped with an overhead mechanical paddle (teflon) stirrer, thermometer, and water cooled condenser fitted with a nitrogen inlet was initially charged with 40.0 gms of a Hudson Falls (containing Aroclor 1242) post-organic sponge regenerated sample in 2-propanol, potassium formate (0. 711 gm, 8.45 mmol=4.5 fold molar excess based upon the number of C—Cl bonds present), potassium hydroxide (0.10 gm, 1.8 mmol), and water (5.0 gm, 0.28 mol). The reaction mixture was stirred at room temperature until complete dissolution of potassium formate had been achieved. The point at which the solution was homogeneous was labelled time=0 for kinetic purposes. A sample (0.2 mL) was removed at this point ($T_o$) and diluted with 2.0 mL of acetonitrile for HPLC analysis. The palladium on carbon (0.018 g, 0.017 mmol; with Pd:C—Cl bonds=1:111) was added to the flask at room temperature. The flask was emersed into a 70° C. heated oil bath. The reaction was sampled every 15 minutes for two hours and after that time sampling was performed at two hour intervals. The reaction was allowed to reflux for 27 hours before cooling to room temperature with HPLC analysis showing 40% formation of biphenyl. A second addition of potassium formate (one third of the initial addition of potassium formate or 1.5 moles based upon C—Cl bonds: 0.255 gm, 3.0 mmol) increased the formation of biphenyl by 10% after 21 hours with a total reaction time of 48 hours. HPLC analysis determined that significant levels (>5000 ppm) were left in the reaction mixture.

What is claimed is:

1. A method of dechlorination of polychlorinated biphenyls which comprises the steps of:
    admixing said polychlorinated biphenyls with an organic solution selected from the group consisting of an alcohol and water, a dipolar aprotic solvent and water, and an oil and water;
    adjusting the pH of said mixture with a base so as to maintain the mixture at a pH of between about 7.0 and 10.0;
    contacting said mixture with a catalytic amount of a hydrogenation catalyst; and
    adding equal incremental portions portion of an excess molar amount of a non-hydrogen evolving transfer agent selected from the group consisting of sodium formate, potassium formate, cesium formate, and lithium formate, whereby the polychlorinated biphenyls are substantially dechlorinated.

2. A method according to claim 1, wherein alcohol of said alcohol and water solution is selected from the group consisting of alcohols having 1 to about 8 carbons with up to two hydroxy groups, and the water is at least about 5 weight percent with the balance being the alcohol.

3. A method according to claim 2, wherein the alcohol is isopropyl alcohol.

4. A method according to claim 1, wherein the dipolar aprotic solvent of said dipolar aprotic solvent and water selection is acetonitrile or dimethylsulfone, and the water is at least about 5 weight percent with the balance being the dipolar aprotic solvent.

5. A method according to claim 1, wherein oil of said oil and water solution is mineral oil, transformer oil, or an askarel type of oil, and the water is at least about 5 weight percent with the balance being said oil.

6. A method according to claim 1, wherein said base is selected from the group consisting of potassium hydroxide and sodium hydroxide.

7. A method according to claim 1, wherein said hydrogenation catalyst is selected from the group consisting essentially of palladium, platinum, and Raney nickel.

8. A method according to claim 1, wherein said excess molar amount of the hydrogen transfer agent is based upon the number of C—Cl bonds, and is between about 1.5 to 6.5.

9. A method according to claim 1 carried out at a temperature between about 60°-80° C.

10. A method according to claim 9 carried out at a temperature of about 70° C.

* * * * *